United States Patent
Wang et al.

(10) Patent No.: US 11,077,097 B2
(45) Date of Patent: Aug. 3, 2021

(54) USE OF AROMATIC RING DRUG IN INHIBITING KEY TRANSCRIPTION FACTOR OF MALIGNANT MELANOMA

(71) Applicant: SHANGHAI INSTITUTE OF ORGANIC CHEMISTRY, CHINESE ACADEMY OF SCIENCES, Shanghai (CN)

(72) Inventors: Jing Wang, Shanghai (CN); Min Guo, Shanghai (CN); Pengfei Fang, Shanghai (CN); Biao Yu, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 37 days.

(21) Appl. No.: 16/627,144

(22) PCT Filed: Jun. 4, 2018

(86) PCT No.: PCT/CN2018/089792
§ 371 (c)(1),
(2) Date: Dec. 27, 2019

(87) PCT Pub. No.: WO2019/001226
PCT Pub. Date: Jan. 3, 2019

(65) Prior Publication Data
US 2020/0129490 A1    Apr. 30, 2020

(30) Foreign Application Priority Data
Jun. 27, 2017 (CN) .......................... 201710502015.1

(51) Int. Cl.
*A61K 31/443* (2006.01)
*A61P 35/00* (2006.01)

(52) U.S. Cl.
CPC ............ *A61K 31/443* (2013.01); *A61P 35/00* (2018.01)

(58) Field of Classification Search
CPC ................................................... A61K 31/443
USPC ........................................................ 514/336
See application file for complete search history.

(56) References Cited

U.S. PATENT DOCUMENTS

2009/0163545 A1    6/2009    Goldfarb

FOREIGN PATENT DOCUMENTS

WO    2016196591 A1    12/2016

*Primary Examiner* — Taofiq A Solola
(74) *Attorney, Agent, or Firm* — Novick, Kim & Lee PLLC; Bin Lu; Zhi Yang Xue

(57) ABSTRACT

Provided is the use of an aromatic ring drug in inhibiting a key transcription factor of malignant melanoma. In particular, provided is the use of a compound as represented by formula A, or an optical isomer thereof or a racemate thereof, or a solvate thereof, or a pharmaceutically acceptable salt thereof in the preparation of a pharmaceutical composition or preparation. The pharmaceutical composition or preparation is used for: (a) inhibiting a key transcriptional regulatory factor of malignant melanoma, namely MITF (Microphthalmia-associated Transcription Factor); (b) treating MITF-related diseases such as melanoma, pancreatic cancer, skin hypersensitivity and asthma; and (c) regulating physiological activities in which MITF is involved, such as skin whitening. In the formula, each group is as defined in the description.

13 Claims, 2 Drawing Sheets

USE OF AROMATIC RING DRUG IN INHIBITING KEY TRANSCRIPTION FACTOR OF MALIGNANT MELANOMA

FIELD OF THE INVENTION

The present invention relates to the field of medicinal chemistry and specifically, relates to an aromatic ring drug and its use in inhibiting key transcription factor MITF of malignant melanoma.

BACKGROUND OF THE INVENTION

Malignant melanoma is a tumor that originates from melanocytes and is one of malignant tumors which is the most difficult to be treated. Studies have shown that MITF is the most important lineage survival oncogene in malignant melanoma. Melanoma patients with a family genetic history often carry the mutation $MITF_{E318K}$, which blocks the degradation of MITF mediated by SUMO, and activates expression of genes downstream to MITF, thereby causing a carrier with such mutation can be five times more likely to develop melanoma than normal human. Resistance to inhibitors in the MAPK signaling pathway (including VRT11E, AZD6224, PLK4720 and other melanoma treatment drugs) will develop due to overexpression of MITF, thereby promoting tumor recurrence. Inhibiting MITF can effectively inhibit the resistance of melanoma to other targeting drugs and enhance treatment efficiency, but it has no effect on other cells of the body. Inhibiting MITF protein expression can significantly inhibit tumor growth at the cellular level and in mouse models. Therefore, small molecules that specifically target MITF have the potential to inhibit the growth of malignant melanoma and reduce drug resistance. Whether MITF can be specifically and effectively targeted by small molecule compounds has been a hot issue in this field.

MITF is a transcription factor containing a conserved bHLHLz domain, and the study of small molecule probes specifically targeting transcription factors has always been a very challenging hot research field. Because the function of transcription factors depends on protein-protein interface (PPI), the PPI interface is generally around 1500-3000 Å2, and relatively long, hydrophobic and rigid small molecule compounds are necessary for specifically targeting PPI interface, which poses great challenges to the solubility, transmembrane ability and stability of the compounds. Furthermore, most transcription factors lack substrate binding pockets that can be used for designing drug, and small molecule probes can not be screened by substrate analog methods. Because the targeting mechanism is not clear, the design of high-throughput screening models is also a difficulty in screening targeted transcription factor inhibitors. At present, there are no reports on small molecular compounds of clear mechanism that directly target MITF.

Therefore, there is an urgent need in the art for a small molecule compound that can directly target MITF, effectively inhibit the growth of malignant melanoma, and reduce drug resistance.

SUMMARY OF THE INVENTION

The purpose of the present invention is to provide a small molecule compound directly targeting MITF, for treating MITF-related diseases, and regulating physiological activities in which MITF is involved.

In the first aspect of the present invention, a use of a compound of formula A, or an optical isomer, a racemate, a solvate or a pharmaceutically acceptable salt thereof in the preparation of a pharmaceutical composition or preparation is provided, the compound of formula A is used for (a) inhibiting a key transcriptional regulatory factor of malignant melanoma (MITF, Microphthalmia-associated Transcription Factor); (b) treating MITF-related diseases; or (c) regulating physiological activities in which MITF is involved,

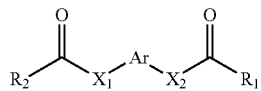

(A)

wherein,
Ar is phenyl, pyridyl, pyrimidinyl, or aromatic ring without or containing nitrogen, sulfur, oxygen heteroatom;
$X_1$ and $X_2$ are each independently selected from the group consisting of O atom, S atom, substituted or unsubstituted N atom, and C atom; wherein the term "substituted" refers to having one or more substituents selected from the group consisting of halogen, —OH, —NH$_2$, —CN, —NH (C1-C3 alkyl), —N(C1-C3 alkyl)$_2$, furan, and substituted or unsubstituted 5-7 membered heterocyclic ring containing O or S heteroatom, wherein the substituted heterocyclic ring contains 1-3 substituents selected from the group consisting of substituted or unsubstituted phenyl, C1-C3 alkyl, C1-C3 haloalkyl, —OH, —NH$_2$, —CN, —NH (C1-C3 alkyl), —N(C1-C3 alkyl)$_2$, halogen, and benzyl;
$R_1$ and $R_2$ are each independently selected from the group consisting of halogen, substituted or unsubstituted C1-C8 alkyl, substituted or unsubstituted C1-C8 alkoxy, substituted or unsubstituted C2-C8 alkenyl, substituted or unsubstituted C2-C8 alkynyl, and substituted or unsubstituted C3-C8 cycloalkyl; wherein the "substituted" refers to having one or more substituents selected from the group consisting of halogen, —OH, —NH$_2$, —CN, —NH (C1-C3 alkyl), —N(C1-C3 alkyl)$_2$, furan, and substituted or unsubstituted 5-7 membered heterocyclic ring containing O or S heteroatom, wherein the substituted heterocyclic ring contains 1-3 substituents selected from the group consisting of substituted or unsubstituted phenyl, C1-C3 alkyl, C1-C3 haloalkyl, —OH, —NH$_2$, —CN, —NH (C1-C3 alkyl), —N(C1-C3 alkyl)$_2$, halogen, and benzyl.

In another preferred embodiment, the compound of formula A has the following structure:

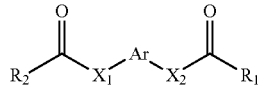

(A)

Wherein,
Ar is pyridyl or benzene ring;
$X_1$ and $X_2$ are each independently selected from the group consisting of N atom, and O atom, S atom;
$R_1$ and $R_2$ are each independently selected from the group consisting of

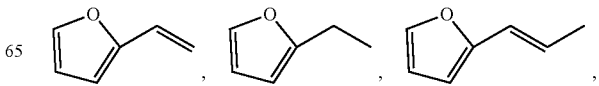

-continued

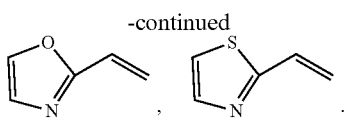

In another preferred embodiment, the compound of formula A has the following structure:

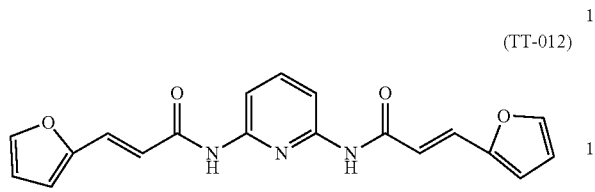

(TT-012)

In another preferred embodiment, the MITF-related diseases are selected from the group consisting of malignant melanoma, pancreatic cancer, skin hypersensitivity, and asthma.

In another preferred embodiment, the physiological activities in which MITF is involved include skin whitening.

In the second aspect of the present invention, a pharmaceutical composition is provided, wherein the pharmaceutical composition comprises (a) an active ingredient comprising a compound of formula A, or an optical isomer, a racemate, a solvate or a pharmaceutically acceptable salt thereof:

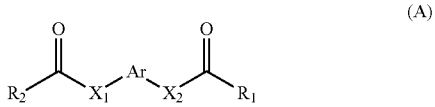

(A)

wherein, Ar, $R_1$, $X_2$, $X_1$ and $X_2$ are defined as in the first aspect of the present invention;

and (b) a pharmaceutically acceptable carrier.

In another preferred embodiment, the pharmaceutical composition or preparation further contain other pharmaceutically active ingredients or pharmaceutically acceptable carriers.

In another preferred embodiment, the pharmaceutical composition contains 0.001-99 wt %, preferably 0.1-90 wt %, more preferably 1-80 wt % of compound of formula A, or an optical isomer, or a racemate, or a solvate or a pharmaceutically acceptable salt thereof, based on the total weight of the composition.

In the third aspect of the present invention, a use of the pharmaceutical composition according to the second aspect of the present invention is provided, wherein the pharmaceutical composition is used for (a) inhibiting a key transcriptional regulatory factor of malignant melanoma (MITF, Microphthalmia-associated Transcription Factor); (b) treating MITF-related diseases; or (c) regulating physiological activities in which MITF is involved.

In the fourth aspect of the present invention, a kit is provided, wherein the kit comprises:

(1) a first container which contains a first pharmaceutical composition, wherein the first pharmaceutical composition comprises a first compound, or an optical isomer, or a racemate, or a solvate or a pharmaceutically acceptable salt thereof, and a pharmaceutically acceptable carrier;

(2) a $n^{th}$ container which contains a $n^{th}$ pharmaceutical composition, wherein the $n^{th}$ pharmaceutical composition comprises a $n^{th}$ compound, or an optical isomer, or a racemate, or a solvate or a pharmaceutically acceptable salt thereof, and a pharmaceutically acceptable carrier; wherein n is any positive integer in 2-8;

wherein the first compound and the $n^{th}$ compound is a compound selected from the group consisting of:

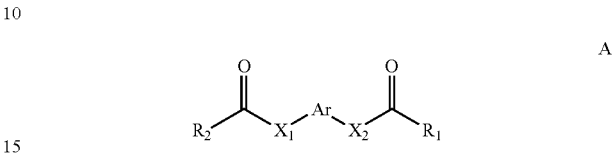

A wherein Ar, $R_1$, $X_2$, $X_1$ and $X_2$ are defined as in the first aspect of the present invention;

and (3) an optional instruction manual.

In the fifth aspect of the present invention, a method for non-therapeutically inhibiting a key transcriptional regulatory factor of malignant melanoma MITF in vitro, which comprises steps of: contacting MITF with a compound of formula A, or an optical isomer, or a racemate, or a solvate or a pharmaceutically acceptable salt thereof to inhibit activity of MITF, wherein the compound of formula A is defined as in the first aspect of the present invention.

In the sixth aspect of the present invention, a method for treating malignant melanoma is provided, which comprises steps of: administering the compound of formula A, or an optical isomer, or a racemate, or a solvate or a pharmaceutically acceptable salt thereof, or the pharmaceutical composition according to the second aspect of the present invention to a subject in need thereof, wherein the compound of formula A is defined as in the first aspect of the present invention.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
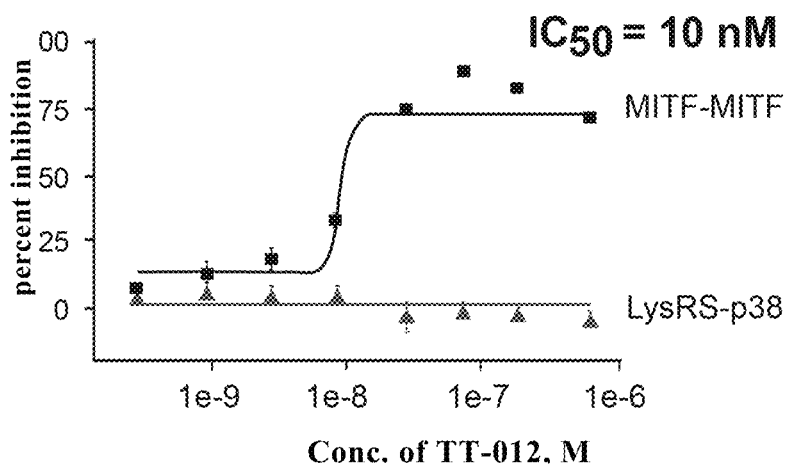
FIG. 1. Compound TT-012 effectively inhibits the formation of dimers of the key transcriptional regulatory factor MITF of malignant melanoma.

Based on a long-term and intensive research, the inventors have firstly found that a class of aromatic compounds of formula A can effectively inhibit the formation of MITF active dimer with $IC_{50}=10$ nM, and significantly directly inhibit activity of MITF active dimer. The experimental results have showed that the compound of formula A has a better inhibiting effect on MITF. The compound of formula A of the present invention can be used to treat malignant melanoma, pancreatic cancer, skin hypersensitivity, asthma and other diseases related to MITF target, and for skin whitening. The inventors have completed the present invention on this basis.

Terms

The term "C1-C8 alkyl" refers to a linear or branched alkyl with 1-8 carbon atoms, such as methyl, ethyl, propyl, isopropyl, 1-butyl, 2-butyl, pentyl, hexyl, heptyl, octyl, or the like.

The term "C3-C8 cycloalkyl" refers to a cycloalkyl with 3-8 carbon atoms, such as cyclopropyl, cyclobutyl, cyclopentyl, cycloheptyl, or the like.

The term "C1-C3 haloalkyl" refers to a linear or branched alkyl with 1-3 carbon atoms substituted by 1-3 halogens.

The term "C1-C8 alkoxy" refers to a linear or branched alkyl with 1-8 carbon atoms, such as methoxy, ethoxy, propoxy, isopropoxy, butoxy, isobutyloxy, sec-butoxy, t-butoxy, or the like.

The term "C2-C8 alkenyl" refers to a linear or branched alkenyl with 2-8 carbon atoms, such as vinyl, propenyl, isopropenyl, 1-butenyl, 2-butenyl, pentenyl, hexenyl, heptenyl, octenyl, or the like.

The term "C2-C8 alkynyl" refers to a linear or branched alkynyl with 2-8 carbon atoms, such as ethynyl, propynyl, isopropynyl, 1-butynyl, 2-butynyl, pentynyl, hexynyl, heptynyl, octynyl, or the like.

The term "5-7 membered heterocyclic ring" refers to a cyclic structure having one or more, preferably 1-3 heteroatoms, and the ring can be a saturated or unsaturated ring.

The term "halogen" refers to F, Cl, Br, and I.

As used herein, the terms "containing" or "comprise (comprising)" can be open, semi-closed, and closed form. In other words, the term further contain "basically consist of" or "consist of".

In the present invention, the term "pharmaceutically acceptable" ingredient refers to a substance suitable for human and/or animals without excessive adverse side effects (such as toxicity, irritation and allergies), i.e., with reasonable benefit/risk ratio.

Malignant Melanoma

Malignant melanoma is a tumor that originates from melanocytes and is one of the malignancies which are most difficult to be treated. Studies have shown that MITF is the most important lineage survival oncogene of melanoma and one of the most breakthrough targets for treating malignant melanoma. 20% of patients with malignant skin cancer have MITF gene amplification. Overexpression of MITF will induce transformation of melanocytes into tumors, and promote tumor proliferation and differentiation.

Microphthalmia-Associated Transcription Factor

The key transcriptional regulatory factor of malignant melanoma (MITF, Microphthalmia-associated Transcription Factor) is the main regulatory factor of epidermal melanocytes of skin, and its function is to regulate the transcription of melanin synthase, promote the production of melanin, and pass it to the surrounding skin keratinocytes to prevent cell damage caused by UV radiation, and form skin surface color at the same time. MITF function loss mutations are the main cause of hereditary albinism disease Waardenburg Syndrome type IIA, Tietz syndrome, and the main reason why people's hair will turn gray during the aging process.

Compound of Formula A

As used herein, "the compound of the present invention", or "the compound of formula A" can be used interchangeably, and refers to a compound of formula A, or a racemate, or a enantiomer or a pharmaceutically acceptable salt thereof. It should be understood that the term also comprises mixtures of the above components.

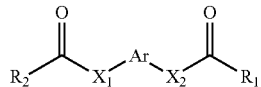

(A)

wherein, each group is defined as above.

In the present invention, a pharmaceutically acceptable salt of compound of Formula A is also included. The term "pharmaceutically acceptable salt" refers to a salt suitable for use as a medicament formed by the compound of the present invention with an acid or base. The pharmaceutically acceptable salts include inorganic and organic salts. Preferred salts are salts formed by the compounds of the present invention and acid. Suitable salt-forming acids include, but are not limited to: inorganic acids such as hydrochloric acid, hydrobromic acid, hydrofluoric acid, sulfuric acid, nitric acid, phosphoric acid, etc; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid, etc; and acidic amino acids such as aspartic acid, glutamic acid.

The compound of formula A in the present invention can be prepared by methods well known to those skilled in the art in the prior art, and the reaction parameters of each step are not specially limited. In addition, typical compounds in the present invention can also be obtained in a commercially available manner.

Unless otherwise specified, all compounds in the present invention are intended to contain all possible optical isomers, such as single chiral compounds, or a mixture of various chiral compounds (i.e., a racemate). Among all the compounds in the present invention, each chiral carbon atom can optionally be R-configuration or S-configuration, or a mixture of R-configuration and S-configuration.

Uses

The compound of formula A in the present invention can be used to inhibit MITF, thereby preventing or treating MITF-related diseases.

The present invention also provides a method for inhibiting MITF and a method for treating MITF-related diseases.

In the present invention, examples of MITF-related diseases include, but are not limited to: malignant melanoma, pancreatic cancer, skin hypersensitivity, asthma and skin whitening, etc.

In one embodiment, a method for non-therapeutically inhibiting the key transcriptional regulatory factor of malignant melanoma MITF in vitro is provided in the present invention, which comprises steps: for example, combining the key transcriptional regulatory factor of malignant melanoma with the compound of formula A (or an optical isomer, or a racemate, or a solvate or a pharmaceutically acceptable salt thereof) to inhibit activity of the key transcriptional regulatory factor of malignant melanoma MITF.

In the present invention, a method for inhibiting the key transcriptional regulatory factor of malignant melanoma MITF is further provided, and the method can be therapeutic or non-therapeutic. Generally, the method comprises the steps: administering the compound of formula A of the present invention to a subject in need thereof. Preferably, the subject includes human and non-human mammals (rodents, rabbits, monkeys, livestock, dogs, cats, etc.).

Composition and Method of Administration

Since the compound of the present invention has excellent inhibiting activity on the key transcriptional regulatory factor of malignant melanoma (MITF, Microphthalmia-associated Transcription Factor), thus the compound, or an optical isomer, or a racemate, or a solvate or a pharmaceutically acceptable salt thereof of the present invention, and the pharmaceutical composition containing the compound of the present invention as main active ingredient can be used to treat, prevent, and alleviate MITF-related diseases. The compound of the present invention can be used for the prevention and treatment of MITF-related diseases such as malignant melanoma, pancreatic cancer, skin hypersensitivity, asthma, skin whitening, etc.

The pharmaceutical composition of the present invention comprises the safe and effective amount of compound of the present invention or a pharmaceutically acceptable salt thereof, and a pharmaceutically acceptable excipient or carrier. Wherein, "safe and effective amount" refers that the amount of the compound is sufficient to significantly improve the condition without serious side effects.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes, but is not limited to: oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizers, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, calcium stearate, magnesium stearate, solid polyethylene glycol, sodium lauryl sulfate, or mixtures thereof. In capsules, tablets and pills, the dosage forms may also contain buffering agent.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds may also be in microencapsulated form with one or more of the above-mentioned excipients.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, and combinations thereof.

Besides these inert diluents, the composition may also contain additives such as wetting agents, emulsifiers, and suspending agent, sweetening agent, flavoring agents and perfume.

In addition to the active compounds, the suspension may contain suspending agent, for example, ethoxylated isooctadecanol, polyoxyethylene sorbitol and sorbitan ester, microcrystalline cellulose, aluminum methoxide and agar, and combinations thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, propellants, and inhalants. The active ingredients are mixed with physiologically acceptable carriers and any preservatives, buffers, or propellants if necessary, under sterile conditions.

Compounds of the present invention can be administrated alone, or in combination with any other pharmaceutically acceptable compounds.

When the pharmaceutical compositions are used, a safe and effective amount of compound of the present invention is administered to a mammal (such as human) in need of treatment, wherein the dose of administration is a pharmaceutically effective dose, the particular dose should also depend on various factors, such as the route of administration, patient healthy status, which are within the skills of an experienced physician.

Compared with the Prior Art, the Main Advantages of the Present Invention Include:

The compound of formula A of the present invention has a significant inhibiting effect on MITF, and the $IC_{50}$ value of inhibiting MITF dimer reaches 10 nm.

(b) The compounds of formula A of the present invention target MITF with a clear action mechanism.

(c) There are good development and application prospects for the compound of formula A of the present invention for treating various diseases related to MITF target.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weigh.

In specific examples, the compound TT-012 is selected to better illustrate the content of the present invention. The compound of TT-012 has the following structural formula, which is one of the compounds of formula A of the present invention:

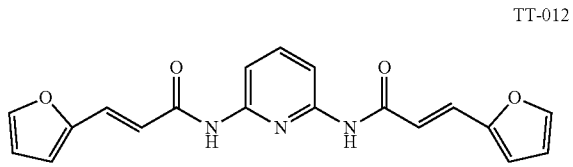 [SMILES: O=C(/C=C/c1ccco1)Nc1cccc(NC(=O)/C=C/c2ccco2)n1]

TT-012

Example 1

TT-012 Effectively and Specifically Inhibited Formation of MITF Dimer.

In the AlphaScreen high-throughput screening model MIDAS (MITF Dependent Alpha-Screen), MITF was labeled with a Biotin tag recognized by Alpha donor beads and a His tag recognized by Alpha receptor beads, respectively. When MITF formed a dimer, Alpha Donor beads and Alpha Receptor beads were pulled close to each other and detected by 680 nM excitation light and 520-620 nM emission light, thereby monitoring the formation of MITF dimer. With MIDAS technology, TT-012 could efficiently inhibit formation of MITF dimer with $IC_{50}=10$ nM (see FIG. 1). FIG. 1 showed that, TT-012 could effectively inhibit formation of MITF dimer with $IC_{50}=10$ nM ((labeled by square) through the high-throughput screening model MIDAS (MITF Dependent Alpha-Screen) test, while not affect the AlphaScreen signal of LysRS-p38 interaction in the control test (labeled by triangle).

Example 2

TT-012 Specifically Inhibited the Transcriptional Activity of MITF

Figure 2:
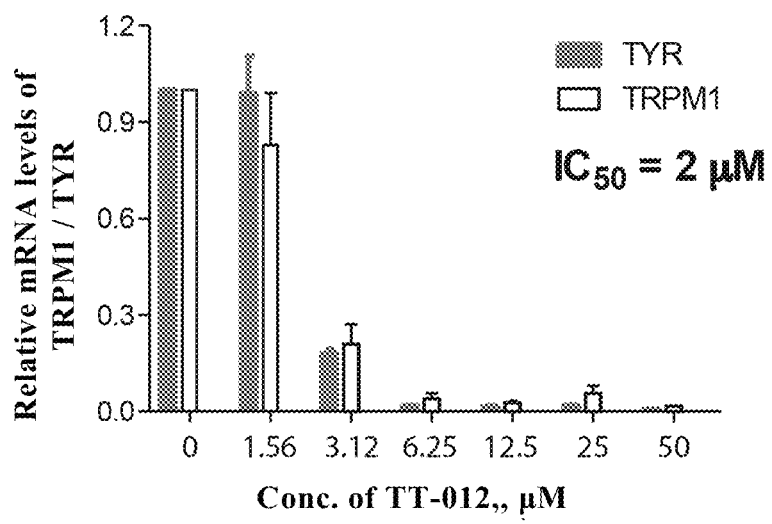
FIG. 2. Compound TT-012 specifically inhibits transcription activity of MITF.

TT-012 was incubated with melanoma cell B16F10 cell line, mRNA was extracted and reverse transcripted, and the transcription of MITF landmark downstream genes-TYR (tyrosinase) and TRPM1 (transient receptor potential cation channel M1) were detected by fluorescent quantitative PCR. TT-012 could effectively inhibit the mRNA levels of MITF landmark downstream genes-TYR and TRPM1 with $IC_{50}=2$ μM through RT-PCR experiments. FIG. 2 showed that active TT-012 could significantly inhibit the transcription of genes downstream to MITF.

Example 3

TT-012 Specifically Inhibited the Growth of Malignant Melanoma

Figure 3:
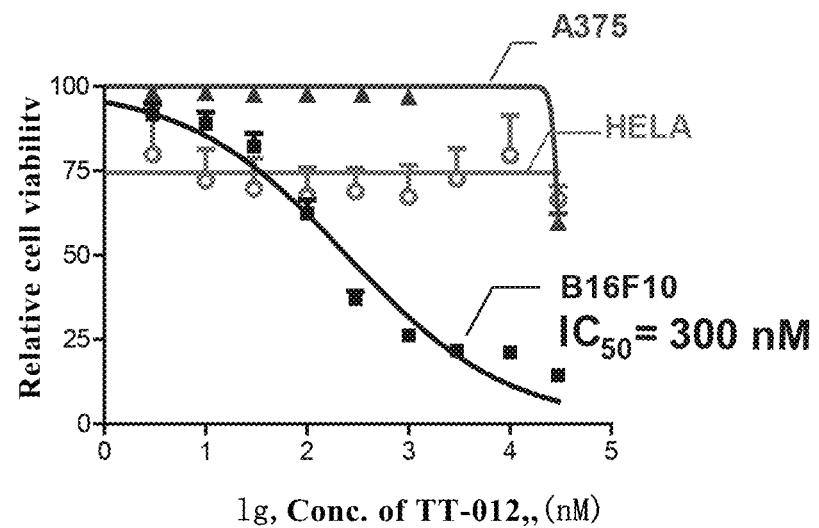
FIG. 3. Compound TT-012 effectively and specifically inhibits the growth of MITF-dependent malignant melanoma cell B16F10.

The active TT012 was incubated with MITF-dependent and highly expressed melanoma cell line B16F10, the melanoma cell line A375 with low expression of MITF, and control cell line Hela, respectively, and cell activity was detected by MTT experiment. As could be seen from FIG. 3, TT-012 could effectively inhibit the growth of MITF-dependent malignant melanoma cells B16F10 with $IC_{50}=300$ nM (labeled by square), but have no killing effects on the melanoma cell line A375 with low expression of MITF (labeled by circle) and control cells HELA (labeled by triangle), suggesting that TT-012 could specifically inhibit MITF activity and inhibit the growth of MITF-dependent malignant melanoma.

Example 4

TT-012 Specifically Inhibited Melanin Formation

Figure 4:
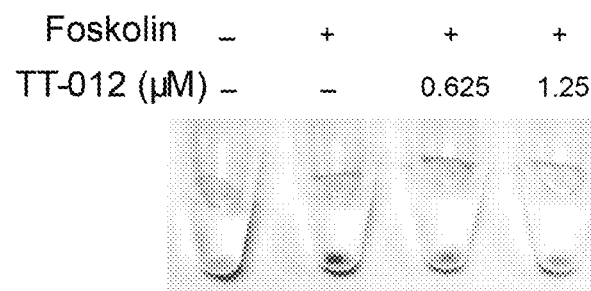
FIG. 4. Compound TT-012 significantly inhibits Forskolin-induced melanin production.

MITF regulated the transcription and expression of melanin synthase TYR, TYRP1, and is the main regulatory factor of melanin formation. Foskolin, a small molecule compound, could regulate pathway, promote the expression of MITF, and promote melanin production by activating MSH-cAMP-CREB. As could be seen from FIG. 4, TT-012 could effectively inhibit the formation of melanin by inhibiting MITF, and had good potential to skin whitening.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:
1. A method for treating a MITF-related disease, which comprises a step of:
administering a compound of formula A, or an optical isomer, or a racemate, or a solvate or a pharmaceutically acceptable salt thereof to a subject in need thereof,

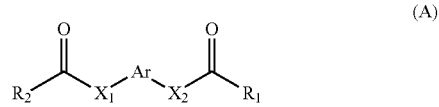

(A)

wherein,
Ar is phenyl, pyridyl, pyrimidinyl, or aromatic ring without or containing nitrogen, sulfur, oxygen heteroatom;
$X_1$ and $X_2$ are each independently selected from the group consisting of O atom, S atom, substituted or unsubstituted N atom, and C atom; wherein the term "substituted" refers to having one or more substituents selected from the group consisting of halogen, —OH, —NH$_2$, —CN, —NH (C1-C3 alkyl), —N (C1-C3 alkyl)$_2$, furan, and substituted or unsubstituted 5-7 membered heterocyclic ring containing O or S heteroatom; wherein the substituted heterocyclic ring contains 1-3 substituents selected from the group consisting of substituted or unsubstituted phenyl, C1-C3 alkyl, C1-C3 haloalkyl, —OH, —NH$_2$, —CN, —NH (C1-C3 alkyl), —N (C1-C3 alkyl)$_2$, halogen, and benzyl;
$R_1$ and $R_2$ are each independently selected from the group consisting of halogen, substituted or unsubstituted C1-C8 alkyl, substituted or unsubstituted C1-C8 alkoxy, substituted or unsubstituted C2-C8 alkenyl, substituted or unsubstituted C2-C8 alkynyl, and substituted or unsubstituted C3-C8 cycloalkyl; wherein the "substituted" refers to having one or more substituents selected from the group consisting of halogen, —OH, —NH$_2$, —CN, —NH (C1-C3 alkyl), —N (C1-C3 alkyl)$_2$, furan, and substituted or unsubstituted 5-7 membered heterocyclic ring containing O or S heteroatom;

wherein the substituted heterocyclic ring contains 1-3 substituents selected from the group consisting of substituted or unsubstituted phenyl, C1-C3 alkyl, C1-C3 haloalkyl, –OH, –NH₂, –CN, –NH (C1-C3 alkyl), –N (C1-C3 alkyl)₂, halogen, and benzyl.

2. The method of claim 1, wherein R₁ and R₂ are each independently selected from the group consisting of substituted C1-C8 alkyl, substituted C1-C8 alkoxy, substituted C2-C8 alkenyl, substituted C2-C8 alkynyl, and substituted C3-C8 cycloalkyl; wherein the "substituted" refers to having one or more substituents selected from the group consisting of furan, and substituted or unsubstituted 5-7 membered heterocyclic ring containing O or S heteroatom, wherein the substituted heterocyclic ring contains 1-3 substituents selected from the group consisting of phenyl, C1-C3 alkyl, C1-C3 haloalkyl, –OH, –NH₂, –CN, –NH (C1- C3 alkyl), –N (C1-C3 alkyl)₂, halogen, and benzyl.

3. The method of claim 1, wherein the compound of formula A has the following structure:

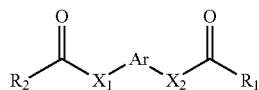

wherein,

Ar is pyridyl or benzene ring;

X₁ and X₂ are each independently selected from the group consisting of N atom, O atom, and S atom;

R₁ and R₂ are each independently selected from the group consisting of

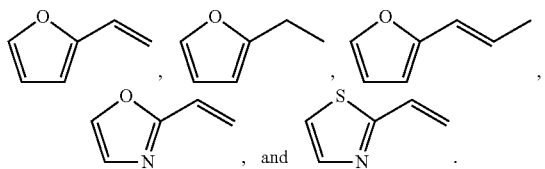

4. The method of claim 1, wherein the compound of formula A has the following structure:

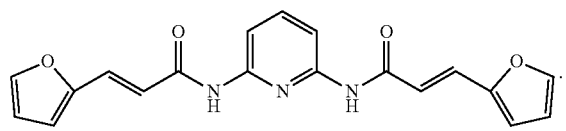 [SMILES: O=C(/C=C/c1ccco1)Nc1cccc(NC(=O)/C=C/c2ccco2)n1]

5. The method of claim 1, wherein the MITF-related disease is selected from the group consisting of malignant melanoma, pancreatic cancer, skin hypersensitivity, and asthma.

6. A method for non-therapeutically inhibiting a key transcriptional regulatory factor of malignant melanoma MITF in vitro, which comprises a step of: contacting MITF with a compound of formula A, or an optical isomer, or a racemate, or a solvate or a pharmaceutically acceptable salt thereof, thereby inhibiting activity of MITF,

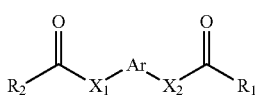

wherein,

Ar is phenyl, pyridyl, pyrimidinyl, or aromatic ring without or containing nitrogen, sulfur, oxygen heteroatom;

X₁ and X₂ are each independently selected from the group consisting of 0 atom, S atom, substituted or unsubstituted N atom, and C atom; wherein the term "substituted" refers to having one or more substituents selected from the group consisting of halogen, –OH, –NH₂, –CN, –NH (C1-C3 alkyl), –N (C1-C3 alkyl)₂, furan, and substituted or unsubstituted 5-7 membered heterocyclic ring containing O or S heteroatom; wherein the substituted heterocyclic ring contains 1-3 substituents selected from the group consisting of substituted or unsubstituted phenyl, C1-C3 alkyl, C1-C3 haloalkyl, –OH, –NH₂, –CN, –NH (C1-C3 alkyl), –N (C1-C3 alkyl)₂, halogen, and benzyl;

R₁ and R₂ are each independently selected from the group consisting of halogen, substituted or unsubstituted C1-C8 alkyl, substituted or unsubstituted C1-C8 alkoxy, substituted or unsubstituted C2-C8 alkenyl, substituted or unsubstituted C2-C8 alkynyl, and substituted or unsubstituted C3-C8 cycloalkyl; wherein the "substituted" refers to having one or more substituents selected from the group consisting of halogen, –OH, –NH₂, –CN, –NH (C1-C3 alkyl), –N (C1-C3 alkyl)₂, furan, and substituted or unsubstituted 5-7 membered heterocyclic ring containing O or S heteroatom;

wherein the substituted heterocyclic ring contains 1-3 substituents selected from the group consisting of substituted or unsubstituted phenyl, C1-C3 alkyl, C1-C3 haloalkyl, –OH, –NH₂, –CN, –NH (C1-C3 alkyl), –N (C1-C3 alkyl)₂, halogen, and benzyl.

7. The method of claim 6, wherein R₁ and R₂ are each independently selected from the group consisting of substituted C1-C8 alkyl, substituted C1-C8 alkoxy, substituted C2-C8 alkenyl, substituted C2-C8 alkynyl, and substituted C3-C8 cycloalkyl; wherein the "substituted" refers to having one or more substituents selected from the group consisting of furan, and substituted or unsubstituted 5-7 membered heterocyclic ring containing O or S heteroatom, wherein the substituted heterocyclic ring contains 1-3 substituents selected from the group consisting of phenyl, C1-C3 alkyl, C1-C3 haloalkyl, –OH, –NH₂, –CN, –NH (C1- C3 alkyl), –N (C1-C3 alkyl)₂, halogen, and benzyl.

8. The method of claim 6, wherein the compound of formula A has the following structure:

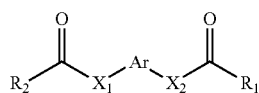

wherein,

Ar is pyridyl or benzene ring;

X₁ and X₂ are each independently selected from the group consisting of N atom, O atom, and S atom;

R₁ and R₂ are each independently selected from the group consisting of

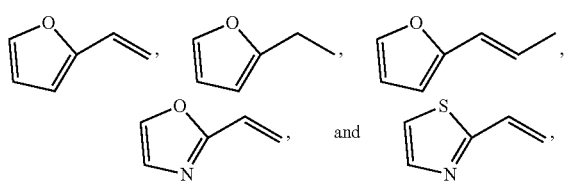

9. The method of claim 6, wherein the compound of formula A has the following structure:

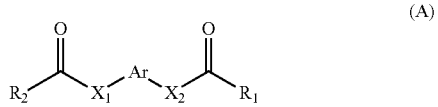

10. A method for inhibiting melanin formation or for whitening skin, which comprises a step of: administering a compound of formula A, or an optical isomer, or a racemate, or a solvate or a pharmaceutically acceptable salt thereof to a subject in need thereof,

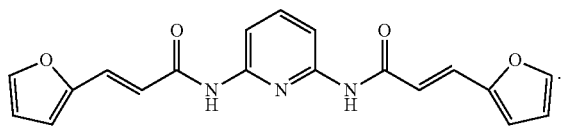 [SMILES: O=C(/C=C/c1ccco1)Nc1cccc(NC(=O)/C=C/c2ccco2)n1]
(A)

wherein,
Ar is phenyl, pyridyl, pyrimidinyl, or aromatic ring without or containing nitrogen, sulfur, oxygen heteroatom;
$X_1$ and $X_2$ are each independently selected from the group consisting of O atom, S atom, substituted or unsubstituted N atom, and C atom; wherein the term "substituted" refers to having one or more substituents selected from the group consisting of halogen, –OH, –NH$_2$, –CN, –NH (C1-C3 alkyl), –N (C1-C3 alkyl)$_2$, furan, and substituted or unsubstituted 5-7 membered heterocyclic ring containing O or S heteroatom; wherein the substituted heterocyclic ring contains 1-3 substituents selected from the group consisting of substituted or unsubstituted phenyl, C1-C3 alkyl, C1-C3 haloalkyl, –OH, –NH$_2$, –CN, –NH (C1-C3 alkyl), –N (C1-C3 alkyl)$_2$, halogen, and benzyl;
$R_1$ and R2 are each independently selected from the group consisting of halogen, substituted or unsubstituted C1-C8 alkyl, substituted or unsubstituted C1-C8 alkoxy, substituted or unsubstituted C2-C8 alkenyl, substituted or unsubstituted C2-C8 alkynyl, and substituted or unsubstituted C3-C8 cycloalkyl; wherein the "substituted" refers to having one or more substituents selected from the group consisting of halogen, –OH, –NH$_2$, –CN, –NH (C1-C3 alkyl), –N (C1-C3 alkyl)$_2$, furan, and substituted or unsubstituted 5-7 membered heterocyclic ring containing O or S heteroatom; wherein the substituted heterocyclic ring contains 1-3 substituents selected from the group consisting of substituted or unsubstituted phenyl, C1-C3 alkyl, C1-C3 haloalkyl, –OH, –NH$_2$, –CN, –NH (C1-C3 alkyl), –N (C1-C3 alkyl)$_2$, halogen, and benzyl.

11. The method of claim 10, wherein $R_1$ and $R_2$ are each independently selected from the group consisting of substituted C1-C8 alkyl, substituted C1-C8 alkoxy, substituted C2-C8 alkenyl, substituted C2-C8 alkynyl, and substituted C3-C8 cycloalkyl; wherein the "substituted" refers to having one or more substituents selected from the group consisting of furan, and substituted or unsubstituted 5-7 membered heterocyclic ring containing O or S heteroatom, wherein the substituted heterocyclic ring contains 1-3 substituents selected from the group consisting of phenyl, C1-C3 alkyl, C1-C3 haloalkyl, –OH, –NH$_2$, –CN, –NH (C1-C3 alkyl), –N (C1- C3 alkyl)$_2$, halogen, and benzyl.

12. The method of claim 10, wherein the compound of formula A has the following structure:

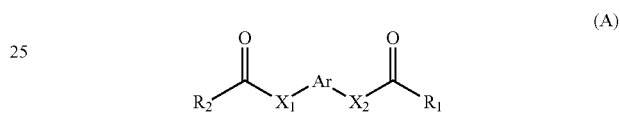
(A)

wherein,
Ar is pyridyl or benzene ring;
$X_1$ and $X_2$ are each independently selected from the group consisting of N atom, O atom, and S atom;
$R_1$ and $R_2$ are each independently selected from the group consisting of

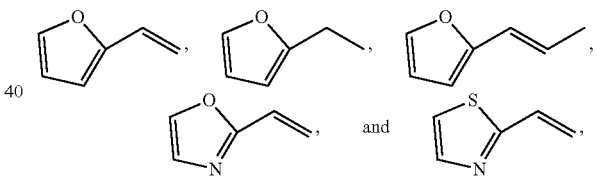

13. The method of claim 10, wherein the compound of formula A has the following structure:

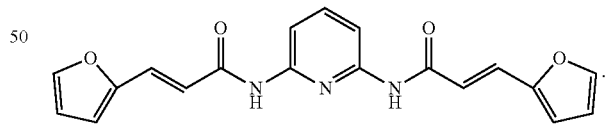

* * * * *